United States Patent [19]
Livingston et al.

[11] Patent Number: 5,301,558
[45] Date of Patent: Apr. 12, 1994

[54] TESTING APPARATUS FOR A MULTILAYER PIEZOELECTRIC ACTUATOR

[75] Inventors: Jeffrey A. Livingston, Wichita, Kans.; Carl A. Kemner, Peoria Heights, Ill.; Chuong Q. Dam, Peoria, Ill.; Jack R. Davis, Peoria Heights, Ill.; Larry C. Clemens, Metamora, Ill.

[73] Assignee: Caterpillar Inc., Peoria, Ill.

[21] Appl. No.: 955,946

[22] Filed: Oct. 2, 1992

[51] Int. Cl.⁵ .................................................. G01L 5/00
[52] U.S. Cl. .................................... 73/862.541; 73/790
[58] Field of Search ................ 73/790, 800, 723, 818, 73/825, 862.541, 862.68, DIG. 4; 250/231.19, 227.21

[56] References Cited

U.S. PATENT DOCUMENTS

| | | | |
|---|---|---|---|
| 4,671,659 | 6/1987 | Rempt et al. | 73/800 |
| 5,195,378 | 3/1993 | Ferguson | 73/790 |

FOREIGN PATENT DOCUMENTS

1560850  4/1990  U.S.S.R. ................................ 73/790

OTHER PUBLICATIONS

NEC Res. & Develop., vol. 32, No. 2, Apr. 1991, "Effects of One-Dimensional Compressive Stress on the Properties of Multilayer Piezoelectric Ceramic Actuator" By Masahiro Kondo and Kazumasa Ohya.
Powder Technology, 22(1979) 271–278, "A High-Pressure Triaxial Testing Cell" W.C.P.M. Meerman and A. C. Knaapen.
Channel Products, Inc., 7100 Wilson Mills Road, Chesterland, Ohio, Data Sheet No. 007-D-001 & Operating Manual For Models CADT-3300 and CADT-B-3000, Belincourt Piezo $D_{33}$ Meter.

Primary Examiner—Richard E. Chilcot, Jr.
Assistant Examiner—William L. Oen
Attorney, Agent, or Firm—David M. Masterson

[57] ABSTRACT

A testing apparatus determines the piezoelectric properties associated with the performance of a multilayer ceramic actuator. The actuator has a predetermined length, $L_1$, and a predetermined cross sectional area, A. The actuator includes an axis and a plurality of piezoelectric elements with electrodes interleaved therebetween. The testing apparatus includes a pressure regulator which controllably supplies pressurized air. A pneumatic cylinder receives the pressurized air and responsively applies axial forces to the actuator. A load cell and associated circuitry measures the applied force on the actuator and responsively produces a force signal, $F_n$. A fiber optic sensor and associated circuitry determines the axial displacement of the actuator and produces a position signal, $L_n$, in response to the magnitude thereof. A computer receives the force signals, $F_n$, and the position signals, $L_n$, and responsively determines the effective modulus of the actuator, $Y_{eff}$.

9 Claims, 7 Drawing Sheets

Fig_1_

Fig_3_

Fig_4_

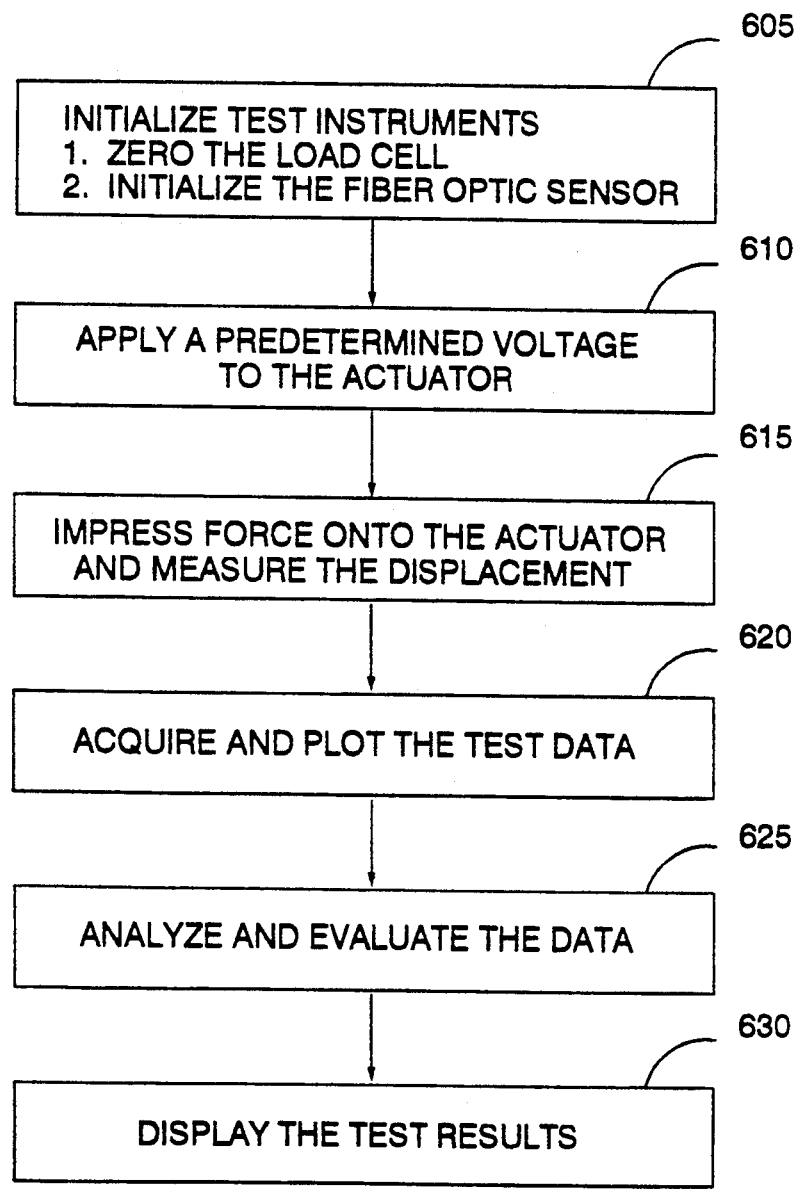
Fig_6_

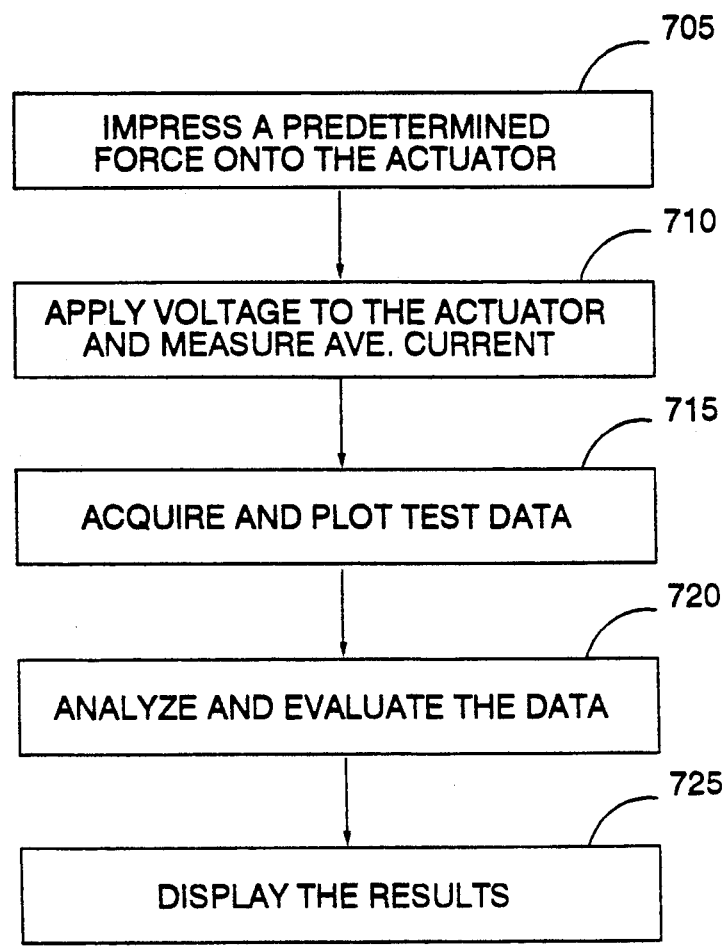

TESTING APPARATUS FOR A MULTILAYER PIEZOELECTRIC ACTUATOR

DESCRIPTION

1. Technical Field

This invention relates generally to a device for testing properties of a piezoelectric actuator and, more particularly, to a device for testing piezoelectric properties of a multilayer piezoelectric actuator.

2. Background Art

Multilayer piezoelectric actuators efficiently transfer electrical energy into mechanical energy. Accordingly, the industrial applications of such piezoelectric actuators is becoming widespread. Because of this widespread use, it is desirous to continually improve the performance of the multilayer piezoelectric actuator. It is well known that the piezoelectric properties associated with the piezoelectric actuator is directly related to its performance. Thus, it is critical to develop a device which tests the piezoelectric properties of the multilayer piezoelectric actuator.

It is common practice in art to modify "generic" testing devices to test piezoelectric properties of multilayer piezoelectric actuators. However such testing devices display poor test repeatability and test accuracy. Typically these testing devices are manual operative; consequently, these devices are labor intensive and introduce human error into the test data.

One example of a "generic" testing device is shown in a paper provided by NEC Res. & Develop., paper Vol. 32, No. 2. April 1991. The paper describes a universal testing machine that is used to test particular piezoelectric properties of a multilayer piezoelectric actuator. For example, the testing machine determines such piezoelectric properties as Young's Modulus. However, certain problems arise when using such a universal testing machine.

First, a spring is used to apply a load on the actuator. It is well known, that as the spring compresses its spring constant changes thus varying the load or force applied to the actuator. Consequently it is difficult for the testing machine to apply a constant load onto the actuator.

Another problem occurs when a "lever-type" electric micrometer is used to measure the length of the piezoelectric actuator. For example, if the length of the center portion of the actuator is not identical to the measuring points of the micrometer, a testing error occurs.

For these reasons, it is apparent that the universal testing machine has an inherent amount of testing error causing poor test repeatability.

The present invention is directed to overcoming one or more of the problems as set forth above.

DISCLOSURE OF THE INVENTION

In one aspect of the present invention, a testing apparatus determines the piezoelectric properties associated with the performance of a multilayer ceramic actuator. The actuator has a predetermined length, $L_1$, and a predetermined cross sectional area, A. The actuator includes an axis and a plurality of piezoelectric elements, N, with electrodes interleaved therebetween. The testing apparatus includes a pressure regulator controllably supplies pressurized air. A pneumatic cylinder receives the pressurized air and responsively applies axial forces to the actuator. A load cell and associated circuitry measures the applied force on the actuator and responsively produces a force signal, $F_n$. A fiber optic sensor and associated circuitry determines the axial displacement of the actuator and produces a position signal, $L_n$, in response to the magnitude thereof. A computer receives the force signals, $F_n$, and the position signals, $L_n$, and responsively determines the effective modulus of the actuator, $Y_{eff}$.

BRIEF DESCRIPTION OF THE DRAWINGS

For a better understanding of the present invention, reference may be made to the accompanying drawings in which:

FIG. 6 illustrates a block diagram of the test procedure for a modulus value associated with the actuator; and FIG. 7 illustrates a block diagram of the test procedure for a capacitance value associated with the actuator.

BEST MODE FOR CARRYING OUT THE INVENTION

Figure 1:
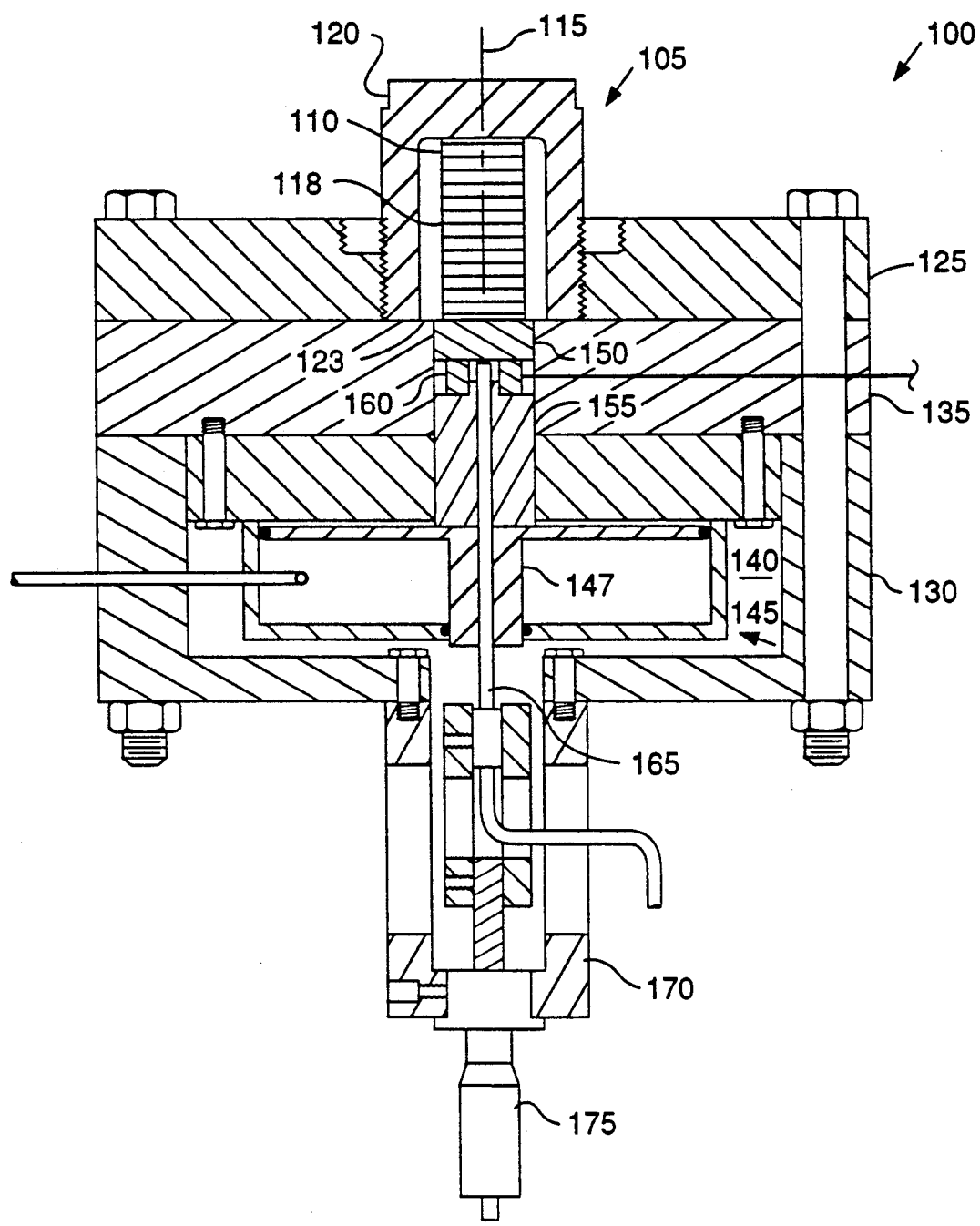
FIG. 1 illustrates an apparatus for testing performance values associated with a multilayered ceramic actuator.

A testing device 100 is depicted in FIG. 1 for testing predetermined piezoelectric properties associated with the performance of a multilayer piezoelectric actuator 105. The actuator 105 includes a plurality of piezoelectric elements 110 formed in a column having a length, $L_1$. As shown, the column of elements 110 is aligned with an axes 115. Each element 110 is in the shape of a disk having a cross sectional area, A. Metallic electrodes 118 are interleaved between the elements 110. The electrodes 118 receive electrical energy for energizing the elements 110. Consequently the energized elements 110 expand axially, proportional to the magnitude of the applied energy. Thus, the actuator 105 is said to transduce electrical energy into mechanical energy.

The actuator 105 includes a housing 120 which surrounds the piezoelectric elements 110. The housing 120 includes a diaphragm 120 attached to an end of the housing 120. The housing 120 serves to protect the actuator 105 and is used to mount the actuator 105 to the testing device 100.

The testing device 100 includes a front plate 125, a rear plate 130, and an intermediate plate 135. The plates are made of hardened steel. The front plate 125 is adapted to receive the actuator 105. The rear plate 130 defines a cavity 140. As shown, a pneumatic cylinder 145 is disposed within the cavity 140 and is rigidly attached to the intermediate plate 135. The air cylinder 145 includes a piston 147.

The front plate 125, intermediate plate 135, and air cylinder 145 define a central bore which is axially aligned with the actuator housing 120. A cylindrical plate 150 is disposed within the central bore of the front plate 125. The cylindrical plate 150 lies adjacent the diaphragm 123 of the actuator housing 120. In the preferred embodiment the cylindrical plate 150 is made of a high tensile steel. Additionally, one end of the cylindrical plate 150 defines a polished surface.

A steel pillow 155 is disposed within the central bore of the intermediate plate 135 and the pneumatic cylinder 145. One end of the pillow 155 is adjacent the piston 147 of the pneumatic cylinder 145. A load cell 160 is disposed between the plate 150 and the other end of the pillow 155. The load cell 160 is formed in a shape of a cylindrical ring and is coaxially disposed about the actuator axis 115. As shown, the pillow 155 and the piston 147 define a small bore which is axially aligned with the actuator axes 115.

A fiber optic sensor 165 is disposed within the small bore. The sensor 165 includes a sensor head located intermediate the polished surface of the cylindrical plate 150. As shown, a sensor housing 170 is fixedly attached to the rear plate 130. The sensor housing 170 includes a micrometer 175 adapted to adjust the sensor head in variable proximity to the cylindrical plate 150.

Figure 2:
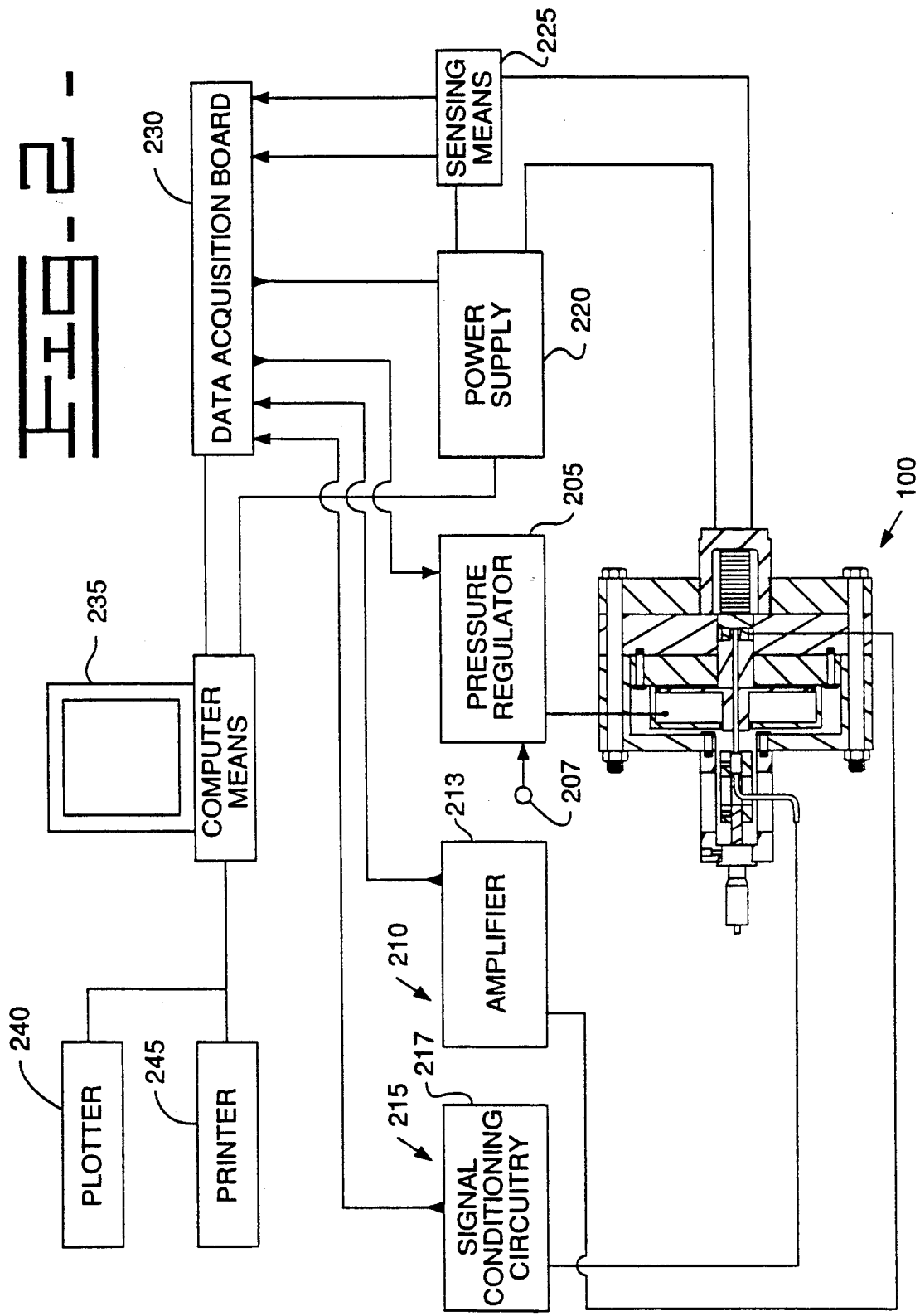
FIG. 2 illustrates a block diagram of the control circuitry associated with the testing device.

A block diagram of the control circuitry associated with the testing device 100 is shown in FIG. 2. A proportional pressure regulator 205 is connected to a source of pressurized air 207. The proportional pressure regulator 205 controllably supplies pressurized air to the pneumatic cylinder 45. The pneumatic device 205 applies axial forces to the actuator 105 in response to receiving the pressurized air. The pneumatic cylinder 145 is manufactured by Mead Fluid Dynamics as Model No. SS-400X0.25 and the pressure regulator 205 is manufactured by proportion-air, Model No. BB-1.

A load means 210 measures the applied force on the actuator 105 and responsively produces a force signal, $F_n$. The load means 210 includes the load cell 160 and a dual mode amplifier 213. For example, the load cell 160 measures the applied force on the actuator 105 and responsively produces a sensed signal. The amplifier 213 receives and conditions the sensed signal. Resultantly the amplifier 213 produces the force signal, $F_n$, having a predetermined voltage range. In the preferred embodiment, the load cell 160 is manufactured by PCB Piezoelectronics Inc., Model No. 211-A and the amplifier 213 is manufactured by Kister, Model No. 5004.

An optical means 215 measures the linear displacement of the actuator 105 and responsively produces a position signal, $L_n$. The optical means 215 includes the sensor 165 and associated signal conditioning circuitry 217. For example, the optical sensor 165 emits random light onto the polished surface of the cylindrical plate 160. The optical sensor 165 senses the reflected light and responsively produces an optical signal. The signal conditioning circuitry 217 receives the optical signal and transposes the optical signal (lumens) to the position signal, $L_n$, having a voltage level proportional to the magnitude of the optical signal. In the preferred embodiment, the fiber optic sensor 165 is a random fiber probe manufactured by Mechanical Technology Instruments as Model No. KDP-032K and the signal conditioning circuitry 217 is manufactured by Mechanical Technology Instruments as Model No. 1000.

A high voltage power supply 220 delivers constant voltage levels to the actuator 105. A sensing means 225 includes a current probe adapted to measure to measure the electrical current flowing through the actuator 105. Additionally, the sensing means 225 may include a voltage probe adapted to measure the voltage applied to the actuator 105. In the preferred embodiment the power supply 220 is manufactured by Trek, Model No. 50/750.

A data acquisition board 235 is connected to the various signal conditioning circuitry. A computer means 235 receives the various signals via the data acquisition board 230 and determines various performance properties of the ceramic actuator 105. Additionally the computer means 235 controls the high voltage power supply 220 and the pressure regulator 213 via the data acquisition board 235. In the preferred embodiment, the data acquisition board is manufactured by Keithlay Metra Byte, as Model No. DA-516. The computer means 235 is an IBM compatible computer which includes data acquisition and statistical software such as Asyst version 3.1 or the like.

A plotter and a printer 240,245 are connected to the computer means 235 for displaying test results.

Figure 3:
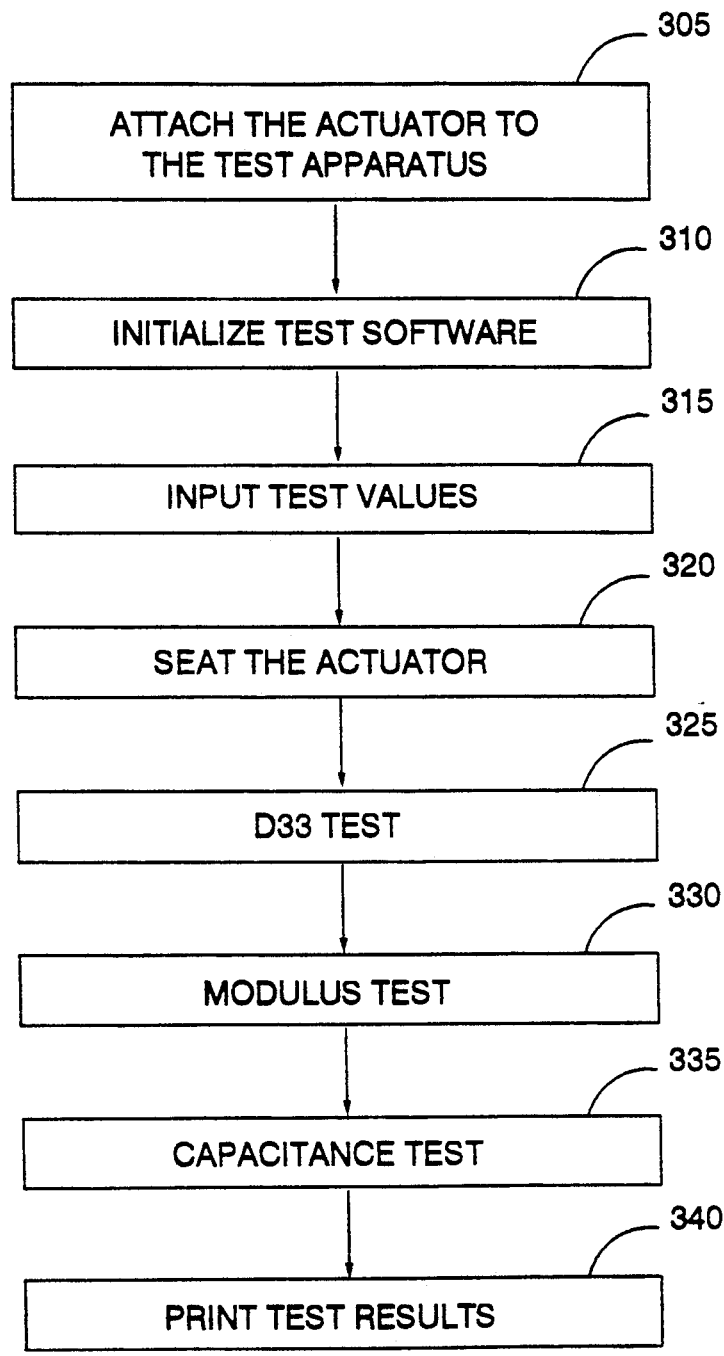
FIG. 3 illustrates a block diagram of the testing procedure associated the testing apparatus.

A general block diagram of the performance test of the piezoelectric actuator 105 is shown in FIG. 3. According to block 305, a laboratory technician attaches the piezoelectric actuator 105 to the testing device 100. Then, as shown in block 310, the technician initializes the testing software. Afterwhich the technician identifies predetermined test values that are associated with the actuator 105, shown by block 315. The test values may include the following:

1. the title of the test
2. the test date
3. the initials of the technician
4. the number associated with the actuator
5. the manner of construction of the actuator
6. the number of hours or cycles of the actuator
7. the number of actuator elements
8. the cross section area of the elements After the technician identifies the test values, the computer means 235 "seats" the actuator 105. For example, the computer means 235 controls the pressure regulator 213 to deliver full pressure to the pneumatic cylinder 145 for a short period of time. Consequently, the pneumatic cylinder 145 applies a force of approximately 900–1000 pounds, for example, to the actuator 105. This force enables the actuator 105 to achieve steady state strain characteristics. This process may be repeated to give the desired results. The test then continues to block 325 where a $D_{33}$ test is performed.

A $D_{33}$ value of the ceramic material is determined in block 320. The $D_{33}$ value represents the electrical activity level of the ceramic material. For example, the $D_{33}$ test value may reveal an amount of expansion of the material with respect to an applied electrical field. After the $D_{33}$ test value has been is determined, a modulus test commences as shown in block 330.

The modulus test determines the effective modulus of the ceramic material. The effective modulus value, $Y_{eff}$, represents the elastic characteristics of the material. Once the effective modulus of the material is determined, a capacitance test commences as shown by block 335.

The capacitance test determines the capacitance of the actuator 105. After the three performance tests are complete, control then transfers to block 340 where the test results are printed in both a graphical and text formats.

Figure 4:
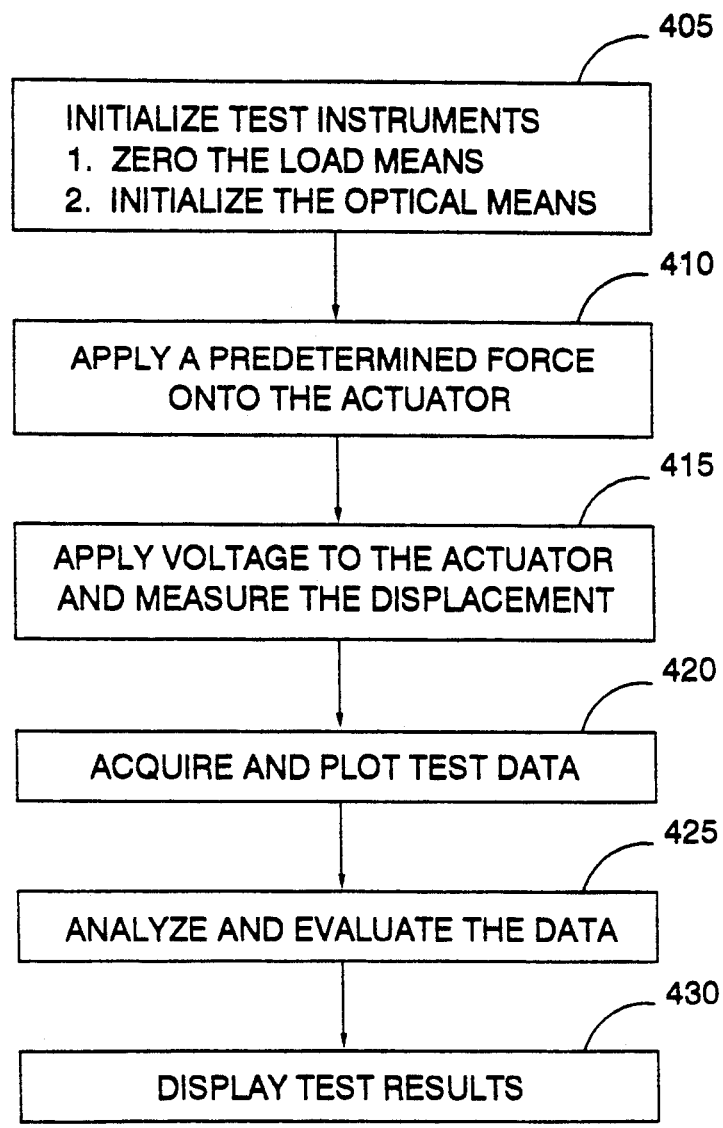
FIG. 4 illustrates a block diagram of the test procedure for a $D_{33}$ value associated with the actuator.

FIG. 4 illustrates a more detailed view of the $D_{33}$ test In block 405 the various test instruments associated with the $D_{33}$ test is initialized.

This includes "zeroing" the load means 210. For example while no force or load is applied to the actuator 105, the amplifier 213 is adjusted to control the magnitude of the force signal, $F_n$, to zero.

Figure 5:
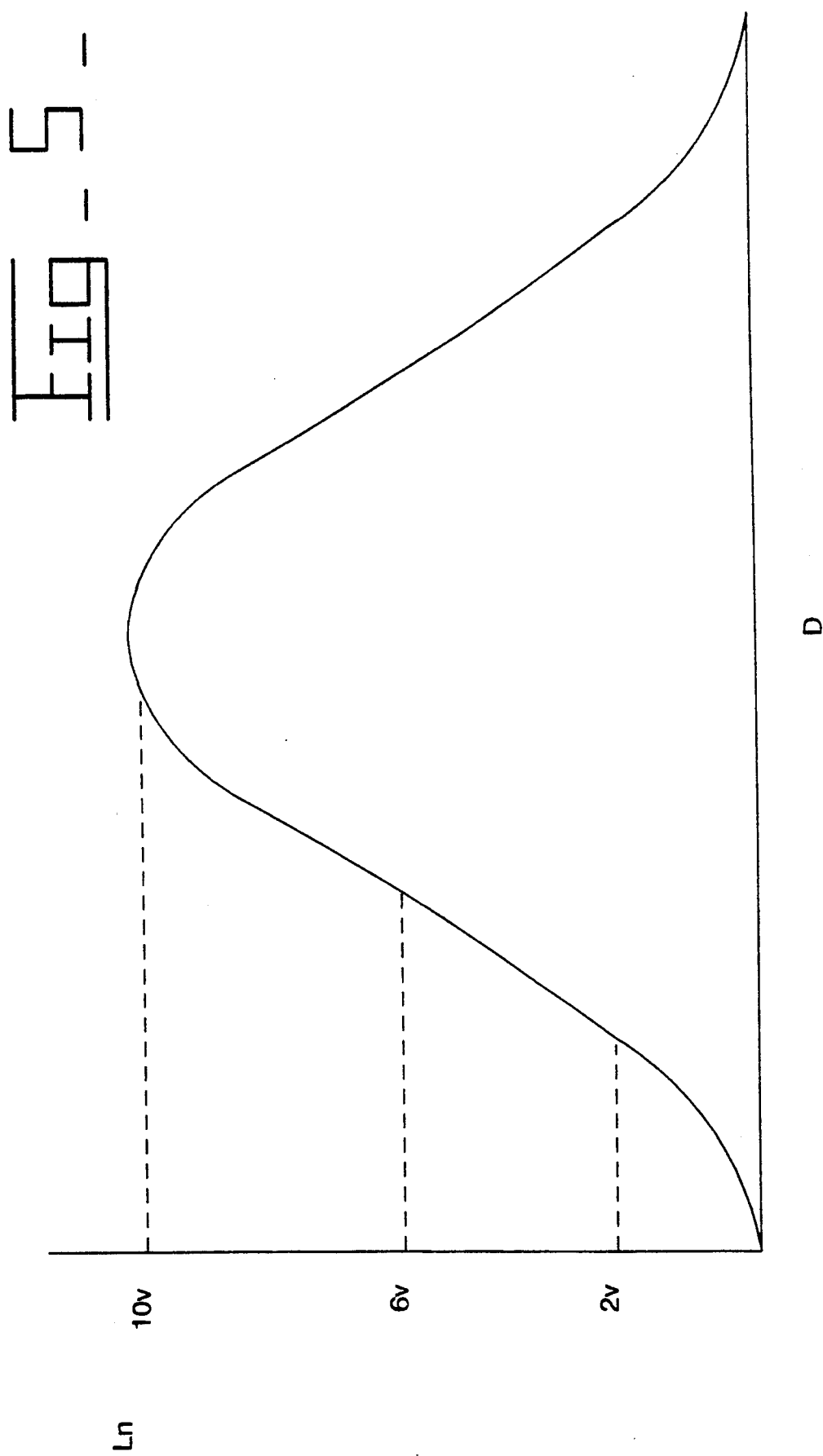
FIG. 5 illustrates a graphical representation of a calibration curve associated with an optical device associated with the testing device.

Next, the signal conditioning circuitry 217 associated with the optical sensor 165 is initialized. This step is best described with reference to FIG. 5. FIG. 5 shows the calibration curve associated with the signal conditioning circuity 217. The horizontal axis denotes the distance, D, the optical sensor head is positioned from the polished surface of the cylindrical plate 150. The vertical axis denotes the magnitude of the position signal, $L_n$, in volts. The position signal is proportional to the magnitude of reflective light that the optical sensor 165 measures. Accordingly, the initialization of the fiber optic sensor 165 consists of the following steps:

A. The technician adjusts the head of the optical sensor with the micrometer until the maximum amount of reflective light is sensed by the optical sensor 165.

B. The technician adjusts the conditioning circuitry 217 to produce a position signal, $L_n$, with a magnitude of 10 volts when the maximum amount of reflectivity is sensed by the optical sensor 165.

It is desirable to adjust the position of the optical sensor 165 so that the measurements occur with respect to the linear portion of the curve. As shown, the linear portion of the curve is bounded by 2V and 6V. Accordingly, after the optical means 215 is initialized, position of the optical sensor 165 is adjusted so that a position signal, $L_n$, is produced with a magnitude of 2 volts while the actuator 105 is energized at 900 V.

The test procedure then proceeds to block 410 where the pneumatic cylinder applies a predetermined force of 250 lbs., for example, onto the actuator 105.

Control then transfers to block 415 where the high voltage power supply 220 delivers a predetermined range of voltages to the actuator 105. For example, the high voltage power supply 220 initially produces a voltage of 200 volts for a predetermined amount of time of 5 sec. The computer means controls the power supply 220 to incrementally deliever voltages to the actuator at 100 volt increments up to 900 volts. The magnitude of the voltage delivered to the actuator 105 is represented by a signal, $V_m$. Further, the actuator 105 displaces a predetermined amount with each incremental increase in voltage. Advantageously, the optical sensor means 215 determines the axial displacement of the actuator 105 and responsively delivers the position signal, $L_m$, to the computer means 235, at each incremental change in voltage.

As illustrated by block 420, the computer means 235 acquires the test data and plots the data for later analysis. For example, the data plot displays the magnitude of the voltage signal $V_m$ vs. the magnitude of the position signal $L_m$. As shown in block 425, once the data is acquired, the data is now ready to be analyzed and evaluated.

The $D_{33}$ value is determined according to the relationship:

$$D_{33} = \frac{|L_{m=o} - L_{m=f}|}{|V_{m=o} - V_{m=f}|} \times 1/N$$

where m is an integer representing the number of measurements at each increment of applied voltage, N represents the number of active or polled piezoelectric discs, o represents the original value and f the final value.

Further the free strain of the actuator, $\epsilon_0$, may be determined as well. For example, the free strain, $\epsilon_0$, is determined by the relationship:

$$\epsilon_0 = \frac{|L_{m=o} - L_{m=f}|}{L_{m=f}}$$

where o represents a measurement at an inital voltage value and f represents a measurement at a final voltage value. For example, the initial position measurement may occur when the actuator is energized at a voltage from a range of 0 to 200 volts and the final position measurement may occur when the actuator is energized with 750 volts.

After the analysis is complete the test results are ready to be displayed, as shown in block 430.

FIG. 6 illustrates a more detailed view of the modulus test. In block 605 load means 210 and optical means 215 are initialized.

The actuator 105 is then energized to 750 volts. The optical sensor 165 is adjusted to produce a position signal, $L_n$, with a magnitude of 2 volts.

The test procedure continues to block 610 where the pneumatic cylinder "seats" the actuator 105. Control then transfers to block 615 where the pneumatic cylinder 145 applies a predetermined range of forces on the actuator 105. For example, the pneumatic cylinder 145 initially produces a force of 250 lbs. for a predetermined amount of time of 5 sec. and incrementally increases the force level to 1000 lbs. at 75 lb increments. The load means 210 measures the force applied to the actuator 105 and delivers a force signal, $F_n$, to the computer means 235, at each incremental change in force. Further, with each incremental increase in force, the actuator 105 compresses a predetermined amount. Advantageously, the optical means 215 determines the axial displacement of the actuator 105 and responsively delivers the position signal, $L_n$, to the computer means 235, at each change in displacement.

As illustrated by block 620, the computer means 235 acquires the test data and plots the data for later analysis. For example, the data plot displays the magnitude of the position signal, $L_m$ vs. the magnitude of the force signal, $F_n$. As shown in block 625, once the data is acquired the data is now ready to be analyzed and evaluated.

The modulus value is determined by the computer means 235 in accordance with the relationship:

$$Y_{eff} = \frac{|F_{n=o} - F_{n=f}|}{|L_{n=o} - L_{n=f}|} \times \frac{L_1}{A}$$

where n is an integer representing the number of measurements at each increment of applied force, o represents the original value and f the final value.

Once the modulus of the actuator 105 is determined, the stall force of the actuator 105 may also be determined according to the following relationship:

$$F_{stall} = (Y_{eff})(A)(\epsilon_0)$$

The stall force may be determined using the determined free strain value or by using the free strain constant that is associated with the ceramic material. The stall force value is associated with the maximum amount of load that the actuator 105 can displace.

After the analysis is complete the test results are displayed, as shown in block 630.

The capacitance of the actuator 105 may also be determined. FIG. 7 illustrates the steps associated with the capacitance test. As shown in block 705 a predetermined force is applied to the actuator 105. The predetermined force may be 250 lbs., for example.

The test proceeds to block 710 where a predetermined voltage range, v, is applied to the actuator 105. For example, the power supply 220 applies a "ramping" voltage from 0 volts to 900 volts to the actuator during a predetermined time period, t, of 200 msec. During this time period the applied current, I, is measured by the sensor means 225, as shown by block 715. Proceeding to block 720 the capacitance is then determined according to the following formula:

$$C = \frac{I_{ave}}{v/t}$$

where $I_{ave}$ is the average current measured by the sensor means 225. After the capacitance has been calculated the results may be displayed, as shown by block 725.

INDUSTRIAL APPLICABILITY

The present invention is directed to an apparatus for determining piezoelectric properties associated with the performance of a multilayer piezoelectric actuator. Shown in FIGS. 3, 4, 5 and 7, are block diagrams of the testing procedures associated with the testing apparatus. As described, the testing apparatus is computer controlled which reduces human error and testing time.

The testing apparatus includes many features which provides accurate test data. One such feature is associated with the pneumatic cylinder. Advantageously, the pneumatic cylinder is adapted to apply axial forces to the actuator at uniform magnitudes. Because the pneumatic cylinder applies a uniform force to the actuator, the resulting test data is accurate.

Another desirable feature of the testing apparatus is associated with placement of the optical sensor. Advantageously, the optical sensor is aligned with the actuator axis. Thus the displacement of the actuator can accurately be measured.

As described, a testing procedure has been developed which accurately quantifies the performance of the multilayer piezoelectric actuator.

Other aspects, objects and advantages of the present invention can be obtained from a study of the drawings, the disclosure and the appended claims.

We claim:

1. A testing apparatus for testing properties of a multilayer ceramic actuator with a predetermined length, $L_1$, and a predetermined cross sectional area, A, the actuator having an axis and a plurality of active piezoelectric elements, N, with electrodes interleaved therebetween, comprising:

a pressure regulator adapted to controllably supply pressurized air;

a pneumatic cylinder adapted to receive the pressurized air and responsively apply constant axial forces to the actuator, each applied axial force having a uniform magnitude;

load cell means for measuring the applied force on the actuator and producing a force signal, $F_n$ in response to the magnitude of the measured force;

a cylindrical plate being disposed adjacent the ceramic actuator;

optical means for emitting random light onto said cylindrical plate, receiving the light reflected from the cylindrical plate and responsively producing a position signal $L_n$, the position signal being indicative of the axial displacement of the actuator; and computer means for receiving said force signals, $F_n$, and said position signals, $L_n$, and responsively determining the effective modulus of the actuator, $Y_{eff}$, according to the relationship:

$$Y_{eff} = \frac{|F_{n=o} - F_{n=f}|}{|L_{n=o} - L_{n=f}|} \times \frac{L_1}{A}$$

where n represents the number of measurements at each increment of applied force, o represents the original value and f the final value.

2. An apparatus, as set forth in claim 1, wherein said load means includes:

a load cell adapted to produce a sensed signal having a magnitude proportional to the applied force on the actuator; and an amplifier adapted to receive and condition the sensed signal and responsively produce the force signal, $F_n$.

3. An apparatus, as set forth in claim 2, wherein said optical means includes:

a fiber optic sensor being axially aligned with the actuator axis and adapted to produce an optical signal in response to receiving the reflected light, the optical signal being representative of the magnitude of reflected light; and a signal conditioning circuit adapted to receive said optical signal and transpose said signal to said position signal, $L_n$, said position signal having a voltage level proportional to the magnitude of the optical signal.

4. An apparatus, as set forth in claim 3, including:

a power supply adapted to apply voltages to the actuator, said computer means including means for controlling said power supply to deliver incremental amounts of voltages to the actuator.

5. An apparatus, as set forth in claim 4, wherein said computer means includes means for receiving said position signals, $L_m$, and responsively determining the electrical activity level of said ceramic actuator, $D_{33}$, according to the relationship:

$$D_{33} = \frac{|L_{m=o} - L_{m=f}|}{|V_{m=o} - V_{m=f}|} \times \frac{1}{N}$$

where $V_m$ represents the magnitude of the applied voltage, m represents the number of measurements at each increment of applied voltage, o represents the original value and f the final value.

6. An apparatus, as set forth in claim 5, including a sensor means for measuring the electrical current flowing through the actuator and producing a current signal, I, in response to the magnitude of the measured current.

7. An apparatus, as set forth in claim 6, wherein said computer means includes means for receiving said current signal, I, and responsively determining the capacitance of said ceramic actuator, C.

8. An apparatus, as set forth in claim 5, wherein said computer means includes means determining the free strain of the actuator, $\epsilon_0$, according to the following relationship:

$$\epsilon_0 = \frac{|L_{m=o} - L_{m=f}|}{L_{m=f}}$$

where o represents a measurement at an inital voltage value and f represents a measurement at a final voltage value.

9. An apparatus, as set forth in claim 8, wherein said computer means includes means for determining the stall force of said ceramic actuator, $F_{stall}$, according to the relationship:

$$F_{stall} = (Y_{eff})(A)(\epsilon_0).$$

* * * * *